United States Patent [19]

Yanishevsky

[11] 4,406,159
[45] Sep. 27, 1983

[54] APPARATUS FOR TESTING AND RECORDING THE FREENESS OF PULP

[75] Inventor: Nisson M. Yanishevsky, Kiev, U.S.S.R.

[73] Assignee: Ukrainskoe Nauchnoproizvodstvennoe Obiedinenie Tsell Juloznobumazhnoi Promyshlennosti (Ukrnpobumprom), Kiev, U.S.S.R.

[21] Appl. No.: 300,483

[22] Filed: Sep. 9, 1981

[51] Int. Cl.³ .......................................... G01N 15/00
[52] U.S. Cl. ...................................................... 73/63
[58] Field of Search ..................... 73/63; 162/198, 263

[56] References Cited

U.S. PATENT DOCUMENTS

| 2,346,746 | 4/1944 | Green | 73/63 |
| 2,546,654 | 3/1951 | Qveflander | 73/63 |
| 3,330,151 | 7/1967 | Reinhall | 73/63 |
| 4,089,210 | 5/1978 | Fedorovich et al. | |

OTHER PUBLICATIONS

Article "Special Instruments and Controllers for the Wood-Pulp and Paper Industry" by L. N. Preobrazhensky et al, Moscow, Lesnaya Promyshlennost (Forestry Industry) Publishers, 1972, pp. 107–109, with translation.

Primary Examiner—E. R. Kazenske
Assistant Examiner—Joseph W. Roskos
Attorney, Agent, or Firm—Fleit, Jacobson & Cohn

[57] ABSTRACT

The apparatus comprises a constant level flow receptacle and an immersion type freeness tester having two chambers, namely a filtration chamber provided with a bottom screen portion, and a measurement chamber. A sensing element is placed inside the measurement chamber for determining the level of the liquid passed through the bottom screen portion, and connected to a circuit for measuring this level and for recording the freeness according to this level. The dimensions of the filtration chamber and those of the measurement chamber are so selected that, during the immersion of the freeness tester into the pulp, water is supplied into the filtration chamber at a constant pressure differential between the level of the upper edge of the filtration chamber and the level of the edge of the flow receptacle.

4 Claims, 6 Drawing Figures

APPARATUS FOR TESTING AND RECORDING THE FREENESS OF PULP

BACKGROUND OF THE INVENTION

The present invention relates to devices intended for continuously and automatically testing the freeness of pulp, i.e. its ability to release a portion of its water content through a screen.

The continuity of the process of testing the freeness of pulp should be understood as the output of data characterizing the freeness said testing being carried out by periodical measurements of the latter during a certain period of time at a frequency ensuring a reliable control of the production process.

More specifically, the present invention is concerned with a device for testing and recording the freeness of pulp, said device being designed for mounting on a pulp line and for carrying out measurements of the freeness of the pulp flowing towards a machine manufacturing, e.g., fiber boards, for the purpose of regulating the process of pulp beating.

The fiber boards are manufactured from vegetable fibers by forming a pulp. The length of fibers and particles is of 0.8 to 1.5 mm, and the thickness thereof is of 0.015 to 0.020 mm. Such a mass is known as a free or a coarsely ground mass whose freeness ranges from 8° to 20° SR. For the purposes of the present invention the term "pulp" designates a mass whose freeness does not exceed 20° SR.

Known in the art are devices for testing the freeness of pulp, presenting reliable information on the freeness (1) within the range of 18°-20° to 60°-65° SR. (L. N. Preobrazhensky et al., Spetsialnye pribory i regulyatory tsellyulozno-bumazhnogo proizvodstva, Moscow, 1972, s. 107-108) and (2) within the range of 60°-65° to 97°-98° SR. (U.S. Pat. No. 4,089,210). At present, the freeness of pulps is determined by means of such laboratory testers as Schopper-Riegler and Defibrator-Sekunda. The Schopper-Reigler tester is insufficiently sensitive to changes in the freeness of pulp within the range of 8° to 25° and beyond 90°. The Defibrator-Sekunda tester in this case possesses higher sensitivity, though both the testers are not suitable for continuous operation directly on the pulp line.

The closest to the present invention from the viewpoint of design features is a device for testing and recording the freeness of pulp (U.S. Pat. No. 4,089,210), comprising a flow receptacle for the pulp whose freeness is to be determined, means for passing the pulp into said receptacle, said means communicating with the latter and designed for mounting on the pulp line, and an immersion type freeness tester. The latter comprises a hollow cylindrical body provided with a bottom screen portion for passing liquid from the pulp. The cavity of said body consists of two chambers communicating therebetween (a filtration chamber and a measurement chamber) from which chambers the filtration one has a greater cross-section, said chamber being provided with the bottom screen portion. There is provided a pneumatic system for immersing said tester into the pulp and removing the same from the latter at certain intervals, and a circuit for recording the result of each measurement carrier out by the tester, said circuit obtaining data on the level of liquid within the tester from the magnitude of the hydrostatic pressure measured by an element sensitive to the level of liquid.

In the above described device the filtrate is first supplied into the internal cavity of the tester for determining the freeness at a pressure determined as a difference between the level of the pulp within the constant level receptacle and that of the pulp at the level of the bottom screen portion of the freeness tester when it is immersed into the constant level receptacle.

As the filtrate is supplied into this tester, the hydrostatic pressure of filtration is dropping, i.e. the filtration process is carried out at a variable pressure which fact adversely affects the result of the measurement of the pulp freeness.

Moreover, at present in the production line, circulating water containing large amount of fine fibers is mainly utilized for beating pulp. In the course of testing the freeness of pulp as above described, due to a great pressure differential of filtration at the initial moment, the fine fibers cover the screen surface and then choke the pores of the free pulp, thereby leading to the wrong evaluation of the freeness thereof, and to an error in the determination of said parameter. The above fact makes it difficult to utilize the above described device for monitoring and regulating the process of beating free pulps.

SUMMARY OF THE INVENTION

Therefore, the general object of the present invention is to provide an apparatus for testing and recording the freeness of pulp, ensuring a high measurement accuracy.

Another object of the present invention is to provide an apparatus for testing and recording the freeness of pulp, whose indications are not influenced by fine fibers.

Still another object of the present invention is to provide an apparatus for testing and recording the freeness of pulp, wherein the measurement accuracy is not influenced by pressure oscillation within the pulp line.

The objects set forth and other objects of the present invention are attained by that in an apparatus for testing and recording the freeness of pulp, comprising a constant level flow receptacle containing the pulp to be tested and adapted to be mounted on the pulp line, an immersion type freeness tester comprising a filtration chamber provided with a bottom screen portion, a measurement chamber communicating with the filtration chamber and with the atmosphere and provided with a bottom portion whereto are introduced a sensing element for determining the filtrate level and a drive for periodical immersion and removal of the freeness tester into and from the constant level receptacle, according to the invention, the filtration chamber is defined by a wall having an overflow edge through which the filtration chamber communicates with the measurement chamber, a distance (h) from the bottom screen portion to the overflow edge on the vertical being determined from the following equation:

$$h = H - K(S/S_1),$$

where

H is the depth to which said bottom screen portion is immersed into the pulp flowing through said constant level receptacle;

S is an area of said bottom screen portion;

$S_1$ is a cross-sectional area of the filtration chamber at the overflow edge;

K is a proportionality factor equal to 0.15 to 2.

The above design makes it possible to eliminate the influence of variations in the pressure within the pulp line on the filtrate contained within the measurement chamber since the filtrate is present within the measurement chamber under the environmental conditions (at atmospheric pressure). With the preset $S/S_1$ ratio and h value it is possible to establish such conditions of filtrations where fine fibers will not be drawn between the fibers of a mat formed on the screen bottom of the filtration chamber.

The inventive concept has found a successive embodiment in such an arrangement of a freeness tester wherein means for discharging the filtrate is constructed as a normally closed overflow valve installed in the given portion of the measurement chamber.

The inventive tester has a compact design. The filtration chamber and the measurement chamber are disposed in a single body. A portion of the filtration chamber is surrounded by the measurement chamber and has the form of a pipe from which the filtrate is discharged and, overflowing the pipe edge, gets into the measurement chamber.

The movement of the filtrate along the overflow pipe is determined by a hydraulic resistance encountered by the filtrate in the passage thereof along the overflow pipe prior to overflowing the upper edge of said pipe, since the hydraulic resistance depends on the ratio between the cross-sectional area of the filtration chamber (S) and that of the overflow pipe ($S_1$), therefore the predetermined ratio ($S/S_1$) provided for a desired intensivity of filtration where fine fibers are not drawn between the fibers of a mat formed on the screen bottom of the filtration chamber.

Since the filtrate is present within the measurement chamber at the atmospheric pressure, it is not influenced by pressure variations within the pulp line.

So long as these testers are periodical ones, the measurement chamber is to be emptied prior to next immersion in order to provide for normal operation of the tester. For this end in the given design overflow valves are mounted in the bottom portion of the measurement chamber, said valves opening when the freeness tester is in the upper position thereby resulting in emptying the measurement chamber.

The overflow valve may comprise a spring-loaded pusher extending beyond the freeness tester and provided with an end portion for contacting an end stio in removing the tester from the pulp.

Such a design of the overflow valve for monitoring the latter makes it possible to utilize the drive of the freeness tester, that is no individual drive is required for such a valve.

According to another aspect of the present invention, in the inventive device the measurement chamber further comprises a receptacle for the filtrate discharging from the filtration chamber when the tester is immersed into pulp, said receptacle communicating with the measurement chamber by means of a flexible hose, while means for discharging the filtrate comprises a pivotal means connecting the receptacle for the filtrate with the constant level receptacle, and a connecting rod pivotally coupling the receptacle for the filtrate with the tester drive for overturning the receptacle for the filtrate.

BRIEF DESCRIPTION OF DRAWINGS

The objects set forth and other objects and advantages of the present invention will become more apparent from the following description of embodiments thereof wherein corresponding parts are identified by corresponding reference characters, with reference to accompanying drawings in which.

DESCRIPTION OF THE PREFERRED EMBODIMENT OF THE INVENTION

Figure 1:
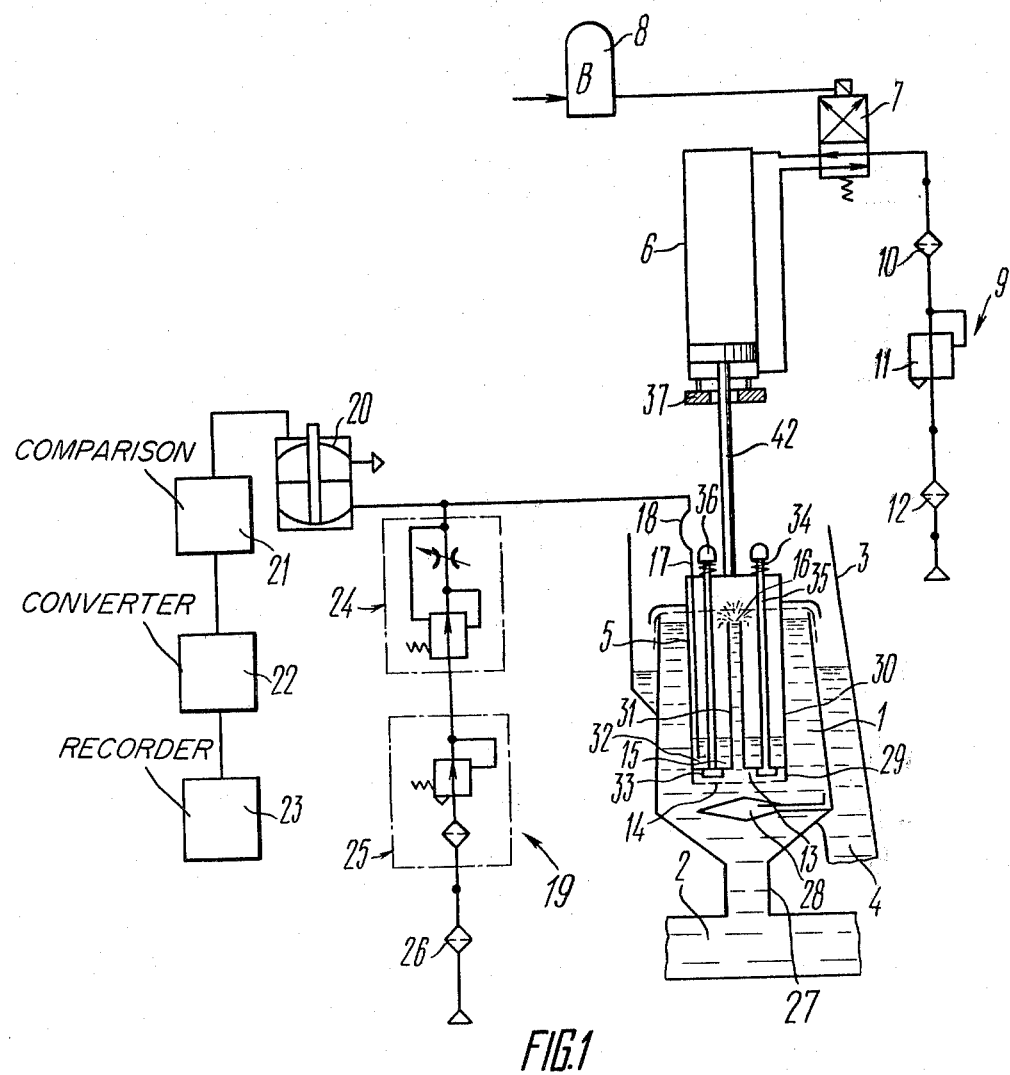
FIG. 1 is a schematic diagram of the inventive object according to one embodiment thereof, illustrating a freeness tester immersed into pulp.

Referring to FIG. 1, a flow receptacle 1 opened in the upper portion thereof is mounted on a pulp line 2 through which pulp is supplied to a machine for manufacturing fiber boards (not shown).

This receptacle is placed into an overflow receptacle 3 which communicates by means of an overflow pipe 4 with the pulp line 2 or with a pulp pool (not shown). As can be seen in FIG. 1, the overflow of the pulp from the overflow receptacle 3 is accomplished at a portion located downstream of the pulp flow towards the machine for manufacturing fiber boards (not shown). It is understood that the pulp is continuously supplied into the flow receptacle 1 from the pulp line 2 and in the course of continuous overflow, gets into the overflow receptacle 3. As a result, a constant level of pulp is maintained within the flow receptacle 1. The pulp contained in the flow receptacle 1 is the pulp whose freeness is to be determined. Being in a continuous motion, this pulp is uninterruptedly renewed within the flow receptacle 1, so the measurements of the freeness are accomplished in the newly supplied and continucously renewed pulp flowing from the pulp line.

An immerson type freeness tester 5 is connected with a means for periodically immersing this tester into the pulp and withdrawing it from said pulp. A device for periodically immersing the freeness tester 5 comprises a fluid-operated working cylinder 6, a distributor 7 controlled by a timer 8 for supplying the fluid into the working cylinder 6, and a source of the pressurized fluid designated by 9.

The most suitable for the purposes of the present invention is a pneumatic driving system of the freeness tester 5 for immersing the latter into the pulp and withdrawing therefrom, though it should not be understood that the invention is limited to only such a drive of the freeness tester, since it is obvious for those skilled in the art that other driving systems can be utilized as well.

The working cylinder 6 being a portion of the pneumatic driving system of the freeness tester 5 is operatively connected with an electromagnetic air distributor 7. The timer 8 controls the air distributor 7 so that the freeness tester 5 immerses into pulp to a certain depth under the action of the pneumatic cylinder 6 and rises over this pulp after a certain time interval. The above source 9 is designed for preparing air and comprises an oil pulverizer 10, a reducer 11 for monitoring the air pressure, and a filter 12 for purifying the air being supplied into the reducer 11. The pulverizer 10 is conventional and has a hermetically sealed housing containing oil. Air is blown through the oil and fed, through the air distributor 7, to the cylinder 6. In supplying a signal from the timer 8 the air distributor 7 actuates the pneumatic cylinder 6 which causes the freeness tester 5 to be introduced into the pulp contained within the flow receptacle 1, and at this time the freeness is recorded by recording means.

Figure 2:
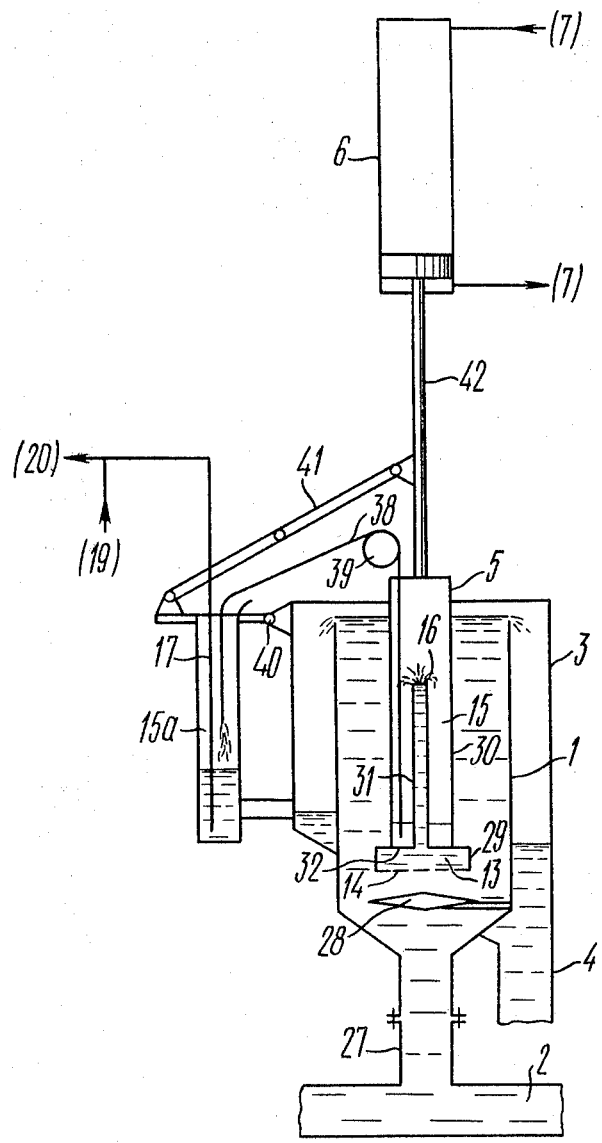
FIG. 2 shows another embodiment of the present invention.
Figure 3:
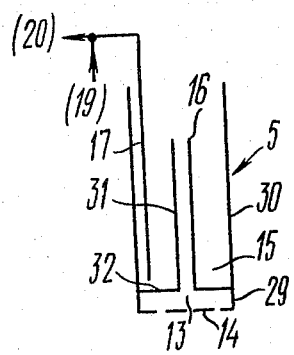
FIGS. 3-6 shows embodiments of the freeness tester of the invention.

The freeness tester 5 is provided with a filtration chamber 13 having a screen bottom portion 14 whose cross-sectional area in the given embodiment decreases from the screen bottom portion 14, and a measurement chamber 15 communicating with the chamber 13 and with the atmosphere, a portion of the measurement chamber 15 being disposed above the filtration chamber 13 (FIGS. 1 and 2). As can be seen in the accompanying drawings, an overflow edge 16 or the interface between the communicating filtration chamber 13 and measurement chamber 15, in the lower position of the freeness tester 5, is located below the level of the edge of the constant level receptacle 1, and a distance (h) from the bottom screen portion (14) to the overflow edge (16) on the vertical is determined from the following equations:

$$h = H - K(S/S_1),$$

where

H is the depth to which the bottom screen portion is immersed into the pump flowing through the constant level flow receptacle;

S is an area of the bottom screen portion;

$S_1$ is a cross-sectional area of the filtration chamber at the overflow edge;

K is a proportionality factor equal to 0.15 to 2.

Into the measurement chamber 15 of the freeness tester 5 is introduced an element which is sensitive to the level of liquid contained in this chamber. The sensitive element can be any means for determining the level known in the art, e.g. a float, electric contacts etc. In the given embodiment of the invention a bubbling pipe 17 is utilized as an element sensitive to the level of liquid, said pipe being introduced into the measurement chamber 15 and connected by a flexible hose 18 with the means for recording the result of each measurement accomplished by the freeness tester 5, and with a source 19 of compressed air supplied into the bubbling pipe 17.

The means for recording the result of each measurement comprises a device for measuring the air pressure, being for example a prior art manometer 20 provided with a differential transformed (not shown), a comparison unit 21 electrically connected wth the manometer 20, a mechanoelectric converter 22 supplying a signal to a recorder 23.

The bubbling pipe 17 is also connected with the source 19 of compressed air, comprising an air flow controller 24 designed for metering the air supplied into the bubbling pipe 17, a pressure reducer 25 and a filter 26.

The operation principle of the system for recording the result of each measurement is based on measuring the static pressure of the liquid layer within the measurement chamber of the freeness tester 5, and is described in detail in the U.S. Pat. No. 4,089,210.

The air pressure within the pipe 17 is measured by the manometer 20. This pressure is supplied to the first of two chambers of the manometer 20 whose second chamber, for the purpose of elimination of the influence of variations in the environment medium, is communicated with the atmosphere.

A change in the pressure difference within the chambers of the manometer 20 causes the shift of the core of the differential transformer (not shown) of this manometer. The above shift results in the change in voltage and phase at the output of the manometer 20 which phenomenon is utilized in the comparison unit 21 for recording the level of liquid contained within the measurement chamber 15.

In the comparison unit 21 are installed a first microswitch (not shown) and a second microswitch (not shown). These microswitches are set for certain values of the liquid levels. Thus, the first microswitch operates when the minimum level is reached within the measurement chamber 15, while the second microswitch operates when the maximum level is reached. The height of the column of liquid from the minimum level to the maximum one constitutes the measurement zone, the level of liquid contained within the filtration chamber 13, i.e. the level formed by liquid flowing through the screen till the formation of the mat being eliminated from the recording. It is to be noted that the minimum level of liquid and the maximum level thereof create correspondingly the minimum and maximum air pressure within the pipe 17.

A unit for processing and delivering the information produces a unified ready signal characterizing the filtration ability of the pulp, i.e. the freeness, since this signal is proportional to the time which has passed between the actuations of the first and second microswitches of the comparison unit 21. A current signal produced by the unit for processing and delivering the information is supplied to the recorder 23; said signal may also be utilized to be supplied to a computer to monitor the freeness of the pulp.

To eliminate errors in the readings of the apparatus of the invention, caused by a hydraulic shock which may appear within the pulp line 2, the flow receptacle is mounted on a transition duct 27 serving as a means for passing the pulp into the flow receptacle 1 and adapted to be mounted on the pulp line 2.

The transition duct 27 is constructed as an expanding cone, i.e. as a structure provided with diverging walls, wherein the cross-sectional area is uniformly increasing in the direction of the pulp flow. It should be noted that such an arrangement of the transition duct is merely illustrative, and other structures may be utilized to obtain the same effect.

Moreover, in the lower portion of the flow receptacle 1 may be mounted a reflector designated by 28 in FIG. 2.

A preferred embodiment of the invention described below is shown in FIG. 1. According to this embodiment, the filtration chamber 13 is provided with a first impermeable peripheral wall 29 constructed integral with a side wall 30 of the measurement chamber 15. In the given example, the filtration chamber 13 in the greatest cross-sectional area thereof has a portion defined by the screen 14 and a cylindrical wall 29, while in the smallest cross-sectional area said chamber has a portion defined by a second impermeable peripheral wall, or an overflow pipe 31 whose level of the upper edge in an interface between these chambers. The filtration chamber 13 and the measurement chamber 15 are also separated by a horizontal wall or a bottom portion 32 of the measurement chamber 15. As can be seen in the figure, the bottom portion 32 of the measurement chamber 15 in this case is located at the portion where the wall 29 transforms into the wall 30.

This junction or the bottom portion 32 is located below the interface between the chambers by a magnitude of the measurement zone plus the level of the filtrate taken from the period of the mat formation. In other words, the interface between the chambers or the edge 16 of the wall 31 is located above the bottom portion 32 of the measurement chamber 15 by the same distance. It is understood that the wall 31 is attached to the bottom portion 32 provided with an opening at the attachment place. The filtration chamber 13 has a cross-sectional area that is largest in the vicinity of the screen bottom 14 and is smaller in the vicinity of overflow edge 16.

In this embodiment of the invention a means for discharging the filtrate is constructed as overflow valves 33 mounted in the bottom portion 32. Each of the overflow valves 33, whose number may be any suitable for the effective operation of the apparatus, comprises a pusher 35 loaded by a spring 34, said pusher extending beyond the tester 5 and being provided with an end portion 36 for contacting an end stop 37 constructed in the given example on the pneumatic cylinder 6.

The apparatus of the invention operates as follows.

At time intervals set by the timer 8, the freeness tester 5 is immersed into the constant level receptacle 1 by means of the pneumatic cylinder 6. The tester 5 is immersed to a predetermined depth, thereby creating a constant pressure applied to the screen bottom 14 of the filtration chamber 13. Following the immersion of the tester 5 into the pulp, the filtrate or the liquid passed through the screen bottom 14 of the filtration chamber 13 fills the latter and is then supplied into the measurement chamber 15 overflowing the edge 16. In this case the process of filtration proceeds at a constant pressure differential, $\Delta H = H - h$, where H is the depth to which the screen 14 of the filtration chamber 13 is immersed into the pulp; h is the vertical distance from the screen 14 to the edge 16 of the wall 31. The motion of the filtrate through the overflow pipe 31 is determined by the hydraulic resistance met by the filtrate in passing through the overflow pipe 31 till the overflow thereof over the upper edge 16 of the pipe 31, since the hydraulic resistance depends upon the ratio between cross-sectional areas of the filtration chamber 13 (S) and the overflow pipe 31 ($S_1$), therefore the preset ratio ($S/S_1$) provides for a desired intensity of filtration at which fine fibers are not drawn between the fibers of the mat formed on the screen bottom of the filtration chamber 13. The measurement of the level of the filtrate within the measurement chamber 15 begins after the formation of a fiber mat under the screen 14, and the variations in the concentration of the pulp stop exerting influence on the measurement results.

Depending on the freeness of the pulp, the intensity of feeding and the amount of the filtrate vary, said variations being recorded by the means for recording the result of each measurement. After the measurement is over, the freeness tester 5 is returned to the upper position by the pneumatic cylinder 6, i.e. said tester is positioned above the level of the pulp. In the course of lift of the tester 5, the end portions 36 of the pushers 35 of the valves 33 abuts against the end stop 37, and the valve 33 opens the measurement chamber 15 for discharging the filtrate, which, when flowing through the screen 14, washes away the fiber mat therefrom. In this position the device is ready for carrying out the next cycle of measurements.

The device of the invention may be also constructed as shown in FIG. 2. According to this embodiment, the device comprises a basically analogous freeness tester 5, although the measurement chamber 15 is provided with a solid bottom portion 32. Besides, the measurement chamber 15 consists of two portions, namely 15 and 15a communicating therebetween by a flexible hose 38 supported, e.g. by a roller 39. As can be seen in FIG. 2, one portion 15 of the measurement chamber is constructed essentially as shown in FIG. 1, while the other portion 15a is disposed outside the constant level receptacle 1, and an element 17 sensitive to the filtrate level is introduced thereinto. The means for discharging the filtrate in the given embodiment comprises a pivotal means 40 connecting the portion 15a of the measurement chamber with the constant level receptacle 1 to ensure turning the portion 15a about the axis of the pivotal means 40. The rotation of the portion 15a is carried out by the drive 6 of the freeness tester 5 for which purpose the portion 15a is pivotally connected with the drive 6 by a connecting rod 41 in the region of a bottom portion 32a.

Proceeding from the method of operation of the above described apparatus of the invention, it is obvious that in the immersion of the freeness tester 5 into the pulp a rod 42, while accomplishing a downward stroke, places the portion 15a of the measurement chamber into the normal position via the connecting rod 41, the measurement being carried out at this moment; and in the removal of the tester 5 out from the pulp the rod 42 turns over the portion 15a via the connecting rod 41, and water is discharged into the receptacle 3.

In another embodiment of the invention the means for discharging the filtrate can be constructed as an electromagnetic valve (not shown) monitored by the timer 8 during the working cycle of the apparatus of the invention.

Thus, the apparatus of the invention allows the sensitivity and measurement accuracy of the freeness of pulps to be upgraded in production lines where circulating water containing fine fibers is utilized. The apparatus further enables carrying out the automatic regulation of the beating process, thereby decreasing power expenditure for beating and increasing the output of products of high quality.

Figure 4:
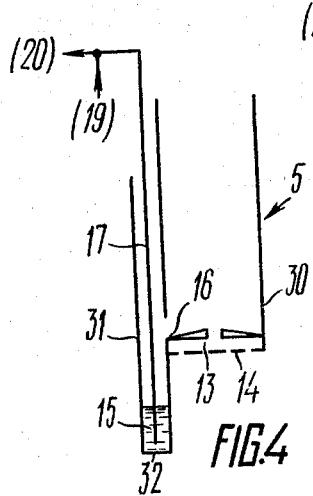
Figure 5:
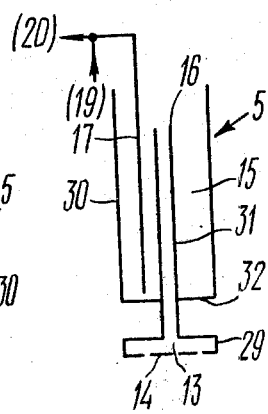
Figure 6:
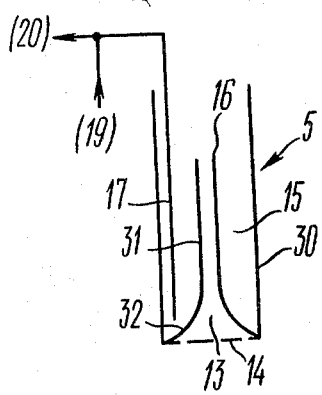

Having described the preferred embodiment of the invention, the applicant does not intend to limit it only to a specific example since other embodiments of the freeness tester are possible, e.g. shown in FIGS. 3 to 6, and those of the means for discharging the filtrate, e.g. in the form of electromagnetic valves, without departing from the spirit and scope of the invention as defined in the appended claims. FIGS. 4 to 6 illustrate alternative orientations of the filtration and measurement chambers with respect to each other.

What is claimed is:

1. An apparatus for testing and recording the freeness of pulp, comprising:
    a constant level flow receptacle containing the pulp to be tested and adapted to be mounted on the pulp line,
    an immersion type freeness tester comprising a first impermeable peripheral wall having an overflow edge and a bottom screen portion both defining a filtration chamber and a second impermeable peripheral wall and a bottom portion together with said first impermeable peripheral wall defining a measurement chamber communicating with the atmosphere and over the overflow edge with said filtration chamber, the overflow edge being separated from said bottom screen portion on the vertical by a distance (h) determined by equation $$h = H - K(S/S_1),$$

where

H is the depth to which said bottom screen portion is immersed into the pulp flowing through said constant level from receptacle;

S is an area of said bottom screen portion;

$S_1$ is a cross-sectional area of the filtration chamber at the overflow edge;

K is a proportionality factor equal to 0.15 to 2;

means for periodically immersing said freeness tester to a fixed depth into the pulp flowing through said constant level flow receptacle and then withdrawing it from the pulp;

a sensing element placed inside said measurement chamber for determining the level of the liquid passed through said bottom screen portion during the immersion of said freeness tester into the pulp and transferred over the overflow edge into said measurement chamber;

means for discharging the liquid from said measurement chamber after each determination of the level thereof.

2. An apparatus as claimed in claim 1, wherein said means for discharging the liquid is a normally closed discharging valve mounted in said bottom portion of said measurement chamber.

3. An apparatus as claimed in claim 2, wherein said discharging valve comprises a spring-loaded pusher extending outside said freeness tester and provided with an end portion, and said means for periodically immersing said freeness tester is a fluid-operated cylinder having an end stop against which the end portion of said pusher abuts when said tester is completely withdrawn from the pulp.

4. An apparatus as claimed in claim 1, wherein the measurement chamber consists of two portions communicating by means of a flexible hose, one portion of the measurement chamber being disposed outside said constant level flow receptacle and said sensing element is introduced thereto, while said means for discharging the liquid comprises a pivot means connecting said portion of the measurement chamber with said constant level flow receptacle, and a connecting rod pivotally connecting said portion of the measurement chamber with said means for periodically immersing said freeness tester for turning over this portion.

* * * * *